United States Patent
Shesol et al.

[11] Patent Number: 5,897,519
[45] Date of Patent: Apr. 27, 1999

[54] INTRAVENOUS SECURING DEVICE AND SECONDARY WOUND DRESSING

[75] Inventors: Barry F. Shesol; Marshall P. Reich, both of Aurora; George Glumac, Montrose, all of Colo.

[73] Assignee: Tapeless Technologies, Inc, Aurora, Colo.

[21] Appl. No.: 08/815,487

[22] Filed: Mar. 11, 1997

[51] Int. Cl.[6] ................................................ A61M 5/00
[52] U.S. Cl. ........................ 602/79; 602/75; 604/179
[58] Field of Search ................................. 602/41, 42, 53, 602/75, 79, 76; 128/888, 887, DIG. 15; 604/179, 180

[56] References Cited

U.S. PATENT DOCUMENTS

| | | | |
|---|---|---|---|
| 3,561,442 | 2/1971 | Goswitz | 602/41 |
| 4,470,410 | 9/1984 | Elliott | 128/877 |
| 4,671,787 | 6/1987 | Widman | 128/DIG. 15 X |
| 5,188,608 | 2/1993 | Fritts | 604/179 |
| 5,403,285 | 4/1995 | Roberts | 604/179 |
| 5,417,646 | 5/1995 | Gauvry | 602/26 |
| 5,449,340 | 9/1995 | Tollini | 602/58 |
| 5,456,660 | 10/1995 | Reich et al. | 602/79 |
| 5,577,516 | 11/1996 | Schaeffer | 602/42 X |
| 5,662,599 | 9/1997 | Reich et al. | 602/79 |
| 5,707,348 | 1/1998 | Krogh | 602/41 |

*Primary Examiner*—Jeanne M. Clark
*Assistant Examiner*—Denise Pothier
*Attorney, Agent, or Firm*—Edwin H. Crabtree; Ramon L. Pizarro; Donald W. Margolis

[57] ABSTRACT

An intravenous securing device and secondary wound dressing for holding intravenous needle tubing and catheter tubing in place in a variety of anatomic locations on the human body. The securing device and secondary wound dressing is used without the need of adhesives. The intravenous securing device and secondary wound dressing consists of an elongated bi-directional wrap stretchable in opposite directions along a length of the wrap. The wrap includes a window opening therethrough which is sufficient in size to allow for visual inspection of the skin entry site of a needle or a catheter without having to remove the wrap. The wrap is washable and reusable. The bi-directional wrap is adaptable for conforming to various parts of the anatomy of a patient and includes releasable hook fasteners at one end of the wrap for securing the wrap around an arm, a hand, a chest, a neck and other parts of the anatomy. The wrap also includes a pair of parallel strips of hook and loop fasteners disposed on opposite sides of the window opening. Intravenous tubing, which is connected to the needle or catheter, is placed between the two parallel strips. When the openings of the two strips are opposed to each other, the strips trap the tubing therebetween for securing the tubing in place without the use of adhesives. By separating the hook and loop fastener parallel strips, the tubing is released.

16 Claims, 2 Drawing Sheets

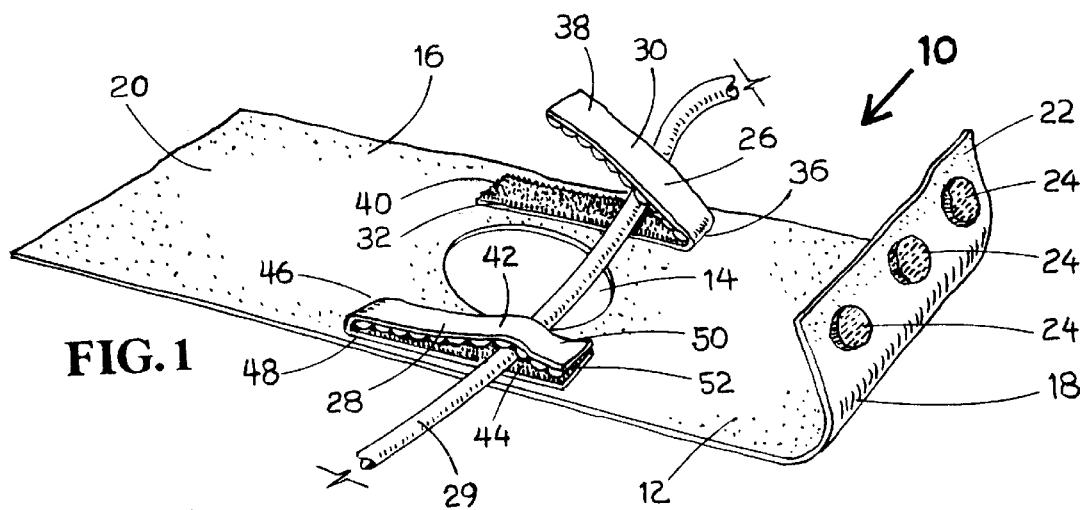
FIG. 1
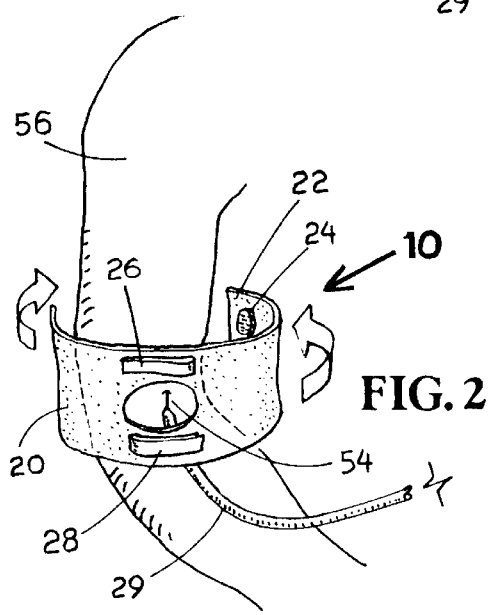
FIG. 2
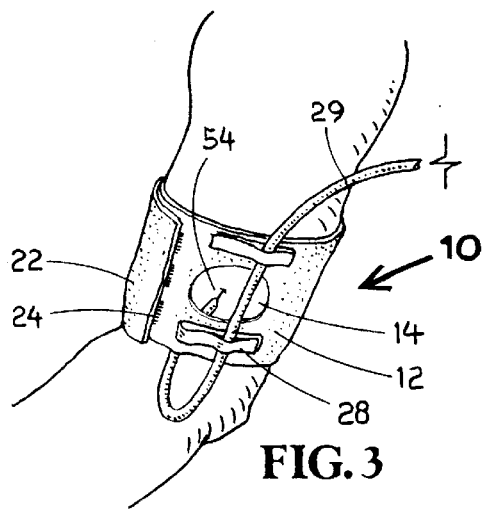
FIG. 3
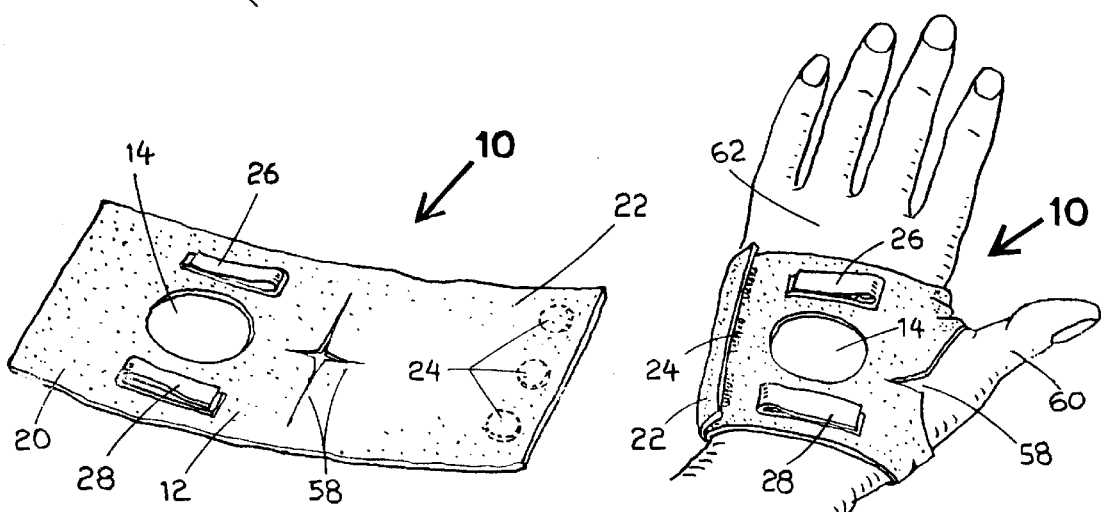
FIG. 4
FIG. 5

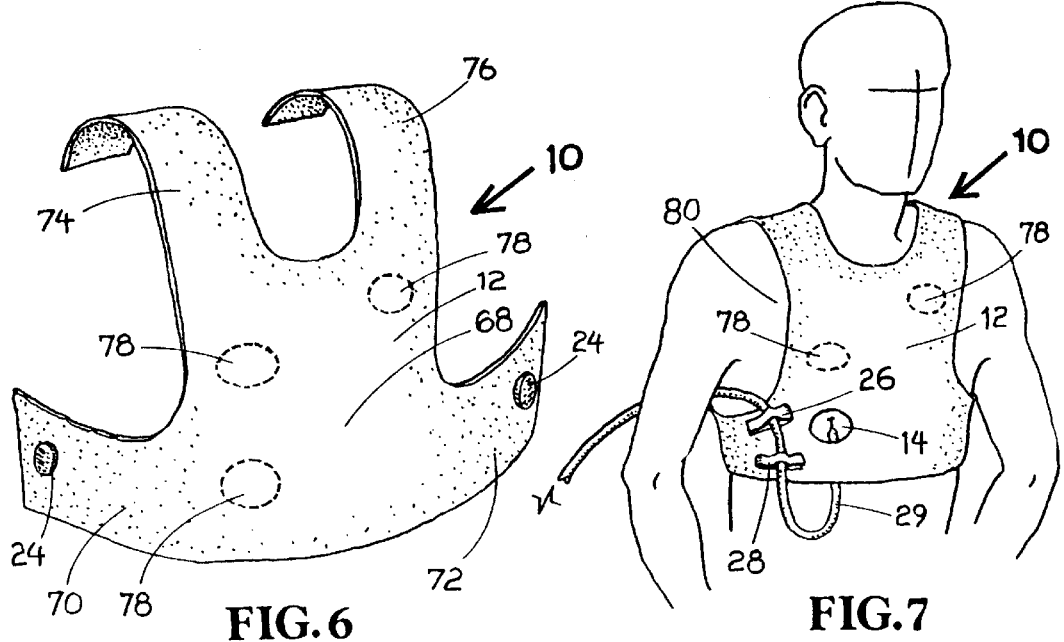
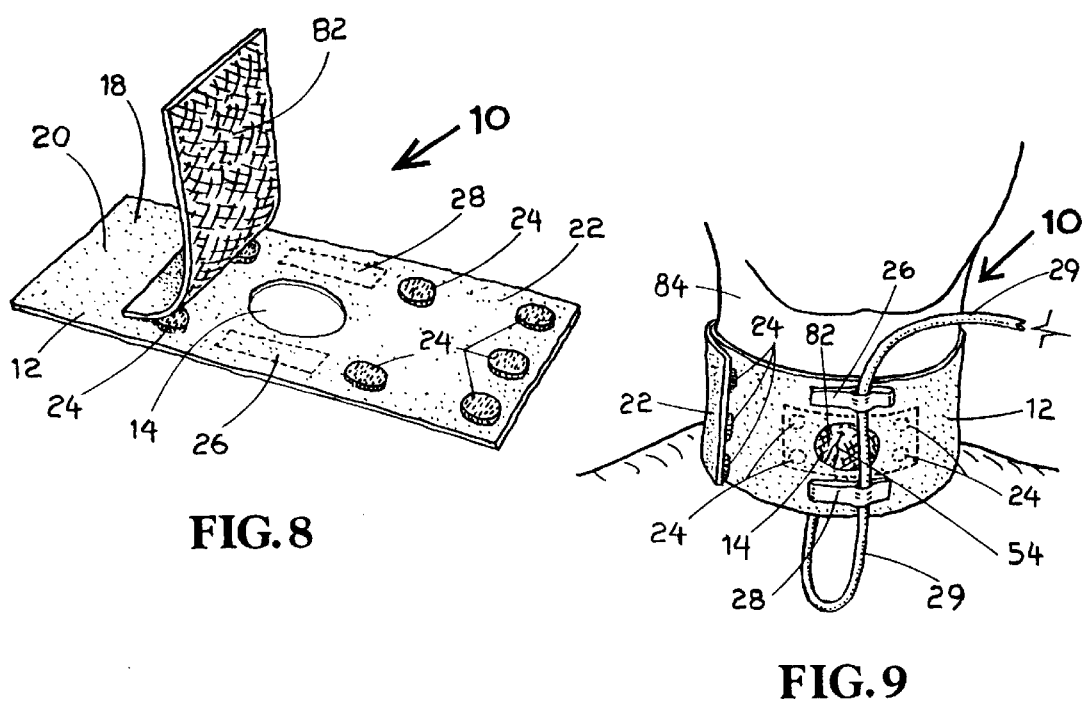

INTRAVENOUS SECURING DEVICE AND SECONDARY WOUND DRESSING

BACKGROUND OF THE INVENTION (a) Field of the Invention

This invention relates to wound dressing wraps and intravenous needle and catheter holding devices and more particularly, but not by way of limitation, to an intravenous securing device for holding an intravenous needle or catheter tubing in place in a variety of anatomic locations.

(b) Discussion of Prior Art

An intravenous catheter or needle is often a life-saving device, and its maintenance is carefully protected since loss of the access to the patient's circulatory system will interrupt necessary nutrition, fluids, medications, cancer fighting substances, and portals of entry for diagnostic procedures. Often the patient's condition, either due to chronic disease or the nature of the medical condition itself, result in a situation where the possibility of finding a new entry site for the IV is limited or impossible. For this reason, the ability to safely secure the intravenous device is a primary concern of the health care provider.

Once the site is located, and the intravenous device hopefully secured to prevent dislodgement, the other essential concern is maintenance of a germ-free environment so infection will not enter the patient via the intravenous portal.

Traditionally, adhesive tape is used to secure the intravenous device in place. This simple method of securing the IV has a significant number of inadequacies and limitations which make an alternative method desirable. These limitations include:

(a) difficulty with conforming to some anatomic locations and contours, particularly in areas of motion.

(b) adhesive allergies resulting in blisters, rashes, open wounds, scars and permanent pigmentation problems.

(c) inability to adhere in areas of raw tissue.

(d) lack of satisfactory adherence in hair-bearing areas.

(e) not reusable.

(f) pain associated with adhesive material removal.

(g) difficult to maintain in a combative patient.

(h) many patients are wet from blood, weather or sweat in an emergency situations, reducing the effectiveness of using adhesive tape.

(i) difficult to apply in areas with adjacent injuries.

(j) complications increase with repeated application of tape.

There are a limited number of alternatives available to secure intravenous devices to avoid adhesives, but none of them address the second major concern, maintaining the sterility and integrity of the insertion site with one device. The intravenous securing device is unique in its ability to meet both concerns with a one unit device. This combination of structure and function results in a novel and superior means of securing intravenous devices.

The subject invention eliminates the deficiencies of other prior art dressing systems by providing in one device the following features:

(a) a reusable, washable, lightweight and non-allergic IV needle tubing and catheter tubing securing system.

(b) ease in application and removal by the health-care provider which is an absolute necessity in an emergency setting.

(c) adaptable and available in different configurations to accommodate a variety of intravenous access sites.

(d) allows visualization of the needle or catheter insertion without having to disrupt the components which secure the needle or catheter.

(e) preserves the integrity of the local skin by avoiding adhesives or abrasive materials.

(f) allows frequent replacement of an occlusive barrier over the needle site with minimal disruption to the site.

(g) provides a method to secure the intravenous tubing without the need for adhesive tapes.

(h) is adaptable to provide a means for securing a secondary dressing, such as gauze, over the insertion site by means of supplemental hook tabs.

All of the above features are included in a one unit device.

In U.S. Pat. No. 5,456,660 issued to two of the subject inventors, a wound dressing support device is described for holding a variety of standard dressings in place on top of an open wound. The support device includes an elongated elastic unidirectional wrap with a window opening therein. This support device does not address the holding of the tubing of an intravenous needle or catheter in place in a variety of anatomic locations.

U.S. Pat. No. 4,732,146 to Fasline et al. discloses a surgical wound dressing device having a frame with an opening for receiving different types of wound dressings. A dressing is held in place by straps attached to one side of the frame with one end of the straps including releasable Velcro fasteners.

U.S. Pat. No. 4,917,112 to Kalt describes a bandage having an opening with the opening covered with a transparent membrane. The membrane is designed to allow air and vapors to permeate outward from the wound and prevent contaminants from entering in the opposite direction.

In U.S. Pat. No. 4,909,243 to Frank et al., a two piece wound dressing is shown having an adhesive layer on one side of a baseplate with an opening in the baseplate to expose the wound and the epithelium area around the wound. A second adhesive layer on one side of a wound pad secures a wound dressing above the opening in the baseplate.

U.S. Pat. No. 4,907,579 to Kum, U.S. Pat. No. 5,167,613 to Karami et al., and U.S. Pat. No. 3,779,242 to McCullough disclosed different types of adhesive bandages for providing open areas to wounds to enhance healing. In U.S. Pat. No. 5,036,838 to Sherman, a foam plastic orthopedic fabric is described having a Velcro tab at one end of the fabric.

In U.S. Pat. No. 4,470,410 to Elliott a stretchable sleeve is shown with Velcro fasteners at the ends of the sleeve. The sleeve includes a central opening with a releasable flap for retaining an intravenous tube or the like.

U.S. Pat. Nos. 4,709,695 to Kohn et al., 4,399,816 to Spangler, 5,086,763 to Hathman, and 4,926,883 to Strock all describe different types of wound surrounding dressings and bandages. Also U.S. Pat. Nos. 4,190,054 to Brennan and 4,658,811 to Beaird disclose stretchable bandages having loop and hook type attachment ends for encircling the head of a patient.

None of the above mentioned prior art patents disclose the unique structure and advantages of the subject invention as described herein when addressing the need of an intravenous securing device for holding intravenous needle tubing and catheter tubing as well as simultaneously providing a secondary wound dressing.

SUMMARY OF THE INVENTION

In view of the foregoing, it is an object of the invention to provide a reusable, washable, lightweight and non-allergic intravenous needle tubing and catheter tubing securing device.

Another object of the securing device is to provide an adaptable bi-directional wrap available in different configurations to accommodate a variety of intravenous access sites.

Still another object of the invention is that the securing device includes a window opening sufficient in size in the elongated wrap which allows visualization of the needle or catheter insertion without having to disrupt the components which secure the needle or catheter.

Yet another key object of the subject securing device is to preserve the integrity of the local skin adjacent the entry site by avoiding the use of adhesives or abrasive materials.

A further object of the invention is to allow frequent replacement of the occlusive barrier over the needle site with minimal disruption to the site.

Also, an object of the securing device is to provide a method to secure the intravenous tubing without the need for adhesive tapes. Further, the invention is adaptable as a secondary wound dressing to provide a means for securing a primary dressing, such as a sterile gauze pad, over the insertion site for providing a protective covering.

The subject intravenous securing device and secondary wound dressing includes an elongated bi-directional wrap stretchable in opposite directions along a length of the wrap. The wrap includes a window opening therethrough which is sufficient in size to allow for visual inspection of the skin entry site without having to remove the wrap. The wrap is washable and reusable. The bi-directional wrap is adaptable for conforming to various parts of the anatomy of a patient and includes releasable hook fasteners at one end of the wrap which attach to the wrap material for securing the wrap around an arm, a hand, a chest, a neck and other parts of the anatomy. The wrap also includes a pair of parallel strips of hook and loop fasteners disposed on opposite sides of the window opening wherein the hook and loop fasteners open at opposite directions. Intravenous tubing, which is connected to a needle or a catheter, is placed between the two parallel strips. When the openings of the two strips are opposed to each other, the hook and loop strips trap the tubing therebetween for securing the tubing in place without the use of adhesives. By separating the hook and loop strips the tubing is released. Hook fasteners may also be disposed around the periphery of the window opening in the wrap for releasable engagement of a primary wound dressing such as a loose weave sterile gauze pad and like dressings.

These and other objects of the present invention will become apparent to those familiar with medical dressings and problems related to the holding of intravenous needle and catheter tubing in place adjacent a skin entry site as outlined in the following detailed description, showing novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a perspective view of the intravenous securing device and secondary wound dressing in the form of an elongated bi-directional wrap with a window opening therethrough. The window opening is sufficient in size for viewing an intravenous needle or catheter. The wrap includes a pair of hook and loop fastener strips for holding intravenous tubing in place.

FIG. 2 is a perspective view of the securing device with the window opening of the wrap positioned above an intravenous needle received in a skin entry in an arm of a patient.

FIG. 3 is a perspective view of the securing device similar to FIG. 2 with the wrap secured to the patient's arm and the hook and loop fastener strips securing the intravenous needle's tubing in place adjacent the window opening.

FIG. 4 is a perspective view of the securing device with a cross cut in one end of the wrap for inserting a thumb of a hand therethrough.

FIG. 5 is a perspective view of the securing device shown in FIG. 4 received on the hand of a patient with the thumb of the hand received through the cross cut in the wrap.

FIG. 6 is a perspective view of the securing device in the wrap in a form of a bib used for receipt around the chest of a patient and having a plurality of possible locations of window openings.

FIG. 7 is a perspective view of the securing device shown in FIG. 6 received around the chest of the patient with a window opening in a lower portion of the wrap and hook and loop fasteners disposed on opposite sides of the window opening.

FIG. 8 is a perspective view of the intravenous securing device and secondary wound dressing wherein a back side of the elongated bi-directional wrap with a window opening includes hook fasteners around the periphery of the window opening for releasably securing a sterile gauze pad.

FIG. 9 is a perspective view of the securing device with the wrap disposed around the neck of the patient. In this drawing, the wrap includes hook fasteners adjacent the window opening for releasably engaging a loose weave sterile gauze pad. The gauze pad when secured to the hook fasteners provides a protective covering over the intravenous needle or catheter.

DESCRIPTION OF THE PREFERRED EMBODIMENTS

In FIG. 1, a perspective view of the intravenous securing device is illustrated and having general reference numeral 10. The securing device 10 includes an elongated stretchable bi-directional wrap 12 with a window opening 14 therethrough for viewing an intravenous needle or catheter. The window opening 14 may be annular or angular in shape and must be of sufficient in size to easily view a skin entry site of either an intravenous needle or a catheter. For example, the window opening diameter may be in a range of 1 to 3 inches or greater depending on the application on the human body.

The wrap 12 is made of a breathable, washable material and is stretchable bi-directionally or in opposite directions along it's length. The wrap 12 includes a front side 16 and a back side 18 with a first end portion 20 and a second end portion 22. The first end portion 20 includes a plurality of hook fasteners 24 on the back side 18 of the wrap. The hook fasteners 24 are used to engage the material of the wrap 12 and along the length of the second end portion 22 when attaching the device 10 on various anatomic locations on the human body as shown in the various drawings.

The wrap 12 also includes a first tube attachment fastener strip 26 and a second tube attachment strip 28 for holding an intravenous tubing 29 in place. A portion of the tubing 29 is shown in FIG. 1. The two tube attachment strips 26 and 28 are disposed on opposite sides of the window opening 14. The first strip 26 includes a loop portion 30 releasably received on top of a hook portion 32. The hook portion 32 is secured to the wrap 12. Also, a first closed end 34 of the loop portion 30 is attached to a first closed end 36 of the hook portion 32 to prevent the complete removal of the loop portion 30 from the hook portion 32. A second open end 38 of the loop portion 30 of the first strip 26 is shown in FIG. 1 in a raised and released position from a second open end 40 of the hook portion 32 for receiving a portion of an intravenous tubing 29 therebetween.

The second strip 28 includes a loop portion 42 releasably received on top of a hook portion 44. The hook portion 44 is secured to the wrap 12. Also, a first closed end 46 of the loop portion 42 is attached to a first closed end 48 of the hook portion 48 to prevent the complete removal of the loop portion 42 from the hook portion 44. A second open end 50 of the loop portion 42 of the second strip 28 is shown in this drawing having been opened and received around a portion of the tubing 29 and then re-engaged to a second open end 52 of the hook portion 44 for attaching and securing the intravenous tubing 29 therebetween.

It should be noted that the first closed end 34 of the loop portion 30 of the first strip 26 is opposed or in an opposite direction to the first closed end 46 of the loop portion 42 of the second strip 28. This important feature prevents the intravenous tubing 29 from pulling loose from both of the tube attachment strips 26 and 28 thus insuring that the tubing 29 will be held in place adjacent the window opening 14 as shown in FIGS. 3 and 9.

In FIG. 2, a perspective view of the intravenous securing device 10 is shown and used as an arm wrap. The device 10 is shown with the window opening 14 of the wrap 12 positioned above an intravenous needle 54 received in a skin entry site in an arm 56 of a patient. A portion of the back side of the wrap 12 in FIG. 2 acts as a means for holding the tube 29 against the human body.

In FIG. 3, the wrap 12 has been secured to the patient's arm 56 using the hook fasteners 24 secured to the second end portion 20 of the wrap 12. Adjustment for tightness of the wrap 12 on the arm 56 can be made by positioning the hook fasteners 24 along the length of the first end portion 20. The intravenous tubing 29 is looped around as shown in FIG. 3 with a portion of the tubing 29 on top of the wrap 12 and received between the two tube attachment strips 26 and 28. The looping of the tubing 29 is a standard safety procedure to help prevent the inadvertent pulling loose of the needle 54. Also the tube attachment strips 26 and 28 will greatly reduce the likelihood of a patient pulling loose the needle 54 or the needle coming loose accidently. Note in this drawing the skin entry site of the needle 54 can be seen for visual inspection.

In FIG. 4, a perspective view of another embodiment of the securing device 10 is shown with the wrap 12 having a cross cut 58 in the second end portion 22 of the wrap 12. The cross cut 58 is used for inserting a thumb 60 of a hand 62 therethrough as shown in FIG. 5.

In FIG. 5, a perspective view of the securing device 10 is shown received around the hand 62 of a patient with the thumb 60 received through the cross cut 58. The intravenous needle 54 and tubing 29 is not shown in this drawings.

In FIG. 6, a perspective view of another embodiment of the securing device 10 is shown with the wrap 12 in a form of a chest wrap 68 with a first waist belt 70 and a second waist belt 72 having hook fasteners 24. The chest wrap 68 also includes a first shoulder strap 74 and a second shoulder strap 76. The chest wrap 68 is secured behind the patient's back, by securing the first waist belt 70 using the hook fasteners 24 to the opposite second shoulder strap 76 and securing the second waist belt using the hook fasteners 24 to the opposite first shoulder strap 74.

Note in this drawing, the chest wrap 68 has a plurality of window opening sites 78 wherein one of the sites 78 can be chosen for a window opening 14 depending on where the intravenous skin entry site will be located on the chest.

In FIG. 7, a perspective view of the securing device 10 is shown received around a chest 80 of a patient with a window opening 14 selected in a lower portion of the wrap 12. The first waist belt 70 is wrapped around the back of the patient and secured to the second shoulder strap 76 in the back of the patient. Likewise, the second waist band 72 is received around the back of the patient and attached to the first shoulder strap 74. As mentioned above, this embodiment of the securing device 10 provides for a number of window opening sites 78 depending on the location of the skin entry site in the chest 80. Also in this drawing, the first and second tube attachment strips 26 and 28 are shown positioned off to the side of the window opening 14 for holding the intravenous tubing 29 in place.

In FIG. 8, another perspective view of the intravenous securing device 10 is shown with the device acting also as a secondary wound dressing. In this drawing, the back side 18 of the wrap 12 is shown with hook fasteners 24 disposed around the periphery of the window opening 14. The hook fasteners 24 are used for releasable engagement with a primary dressing such as a loose weave of a standard cotton sterile gauze pad 82. The sterile gauze pad 82 is used in this example as a primary wound dressing and received over the top of the skin entry site and the intravenous needle 54. When the gauze pad 82 needs to be changed, the first and second end portions 20 and 22 of the wrap 12 are quickly released and the used pad 82 removed from the hook fasteners 24. A fresh sterile gauze pad 82 is then reattached to the fasteners 24. While the gauze pad 82 is shown in this drawings as a primary wound dressings, it can be appreciated that various types of dressing pads can be used equally well and attached to the periphery of the window opening 14 with hook fasteners 24 or an adhesive. Again, it is important to note while an adhesive is mentioned herein for securing a wound dressing, the adhesive or the hook fasteners would never come into contact with the patient's skin and are used only for securing component parts in place.

In FIG. 9, a perspective view of the securing device 10 is shown and used as a secondary wound dressing with the wrap 12 disposed around a neck 84 of the patient. In this drawing, the wrap 12 can be seen with the hook fasteners 24 shown in dotted lines and on the back side 18 of the wrap. The sterile gauze pad 82 is shown received over the intravenous needle 54 and a portion of the intravenous tubing 29. The pad 82 is releasably secured to the hook fasteners 24 adjacent the window opening 14. The gauze pad 82 when secured to the hook fasteners 24 as mentioned above provides a protective covering over the intravenous needle 54 or catheter. Also, while not shown in the drawings, a transparent layer of dressing material can be used and placed over the window opening 14 and secured to the sides of the window opening 14 for holding and sealing the intravenous needle 54 and a portion of the intravenous tubing 29 in place at the skin entry site.

While the invention has been particularly shown, described and illustrated in detail with reference to the preferred embodiments and modifications thereof, it should be understood by those skilled in the art that changes in form and detail may be made therein without departing from spirit and scope of the invention as claimed, except as precluded by the prior art.

The embodiments of the invention for which an exclusive privilege and property right is claimed are defined as follows:

1. An intravenous securing device and secondary wound dressing for holding intravenous tubing in place on a variety of anatomic locations on the human body and holding a primary wound dressing on top of an intravenous needle or catheter inserted into a skin entry site, the needle or catheter connected to the intravenous tubing, the securing device comprising:

an elongated wrap having a front side, a back side, a first end and a second end;

means for securing the first end of said wrap to the second end of said wrap when said wrap is received around a selected location on the human body;

a window opening in said wrap, a center portion of said window opening adapted for receipt over the skin entry site, said window opening sufficient in size for visual inspection of the skin entry site without having to remove said wrap;

means for holding a portion of the intravenous tubing against the human body and adjacent the skin entry site, said means for holding being a portion of the back side of said elongated wrap and disposed next to said window opening; and intravenous tubing offset holding means for releasably securing a portion of the intravenous tubing on the front side of said wrap and adjacent to and offset from the center portion of said window opening for providing a clear view of the skin entry site, said intravenous tubing offset holding means for releasably securing the intravenous tub e substantially parallel to a length of the intravenous needle or catheter inserted into the skin entry site.

2. The securing device as described in claim 1 further including means for securing the primary wound dressing on said wrap, said means for securing disposed around the periphery of said window opening.

3. The securing device as described in claim 1 wherein said means for securing the first end of said wrap to the second end of said wrap is a releasable fastener.

4. The securing device as described in claim 1 wherein said intravenous tubing offset holding means is a pair of tube attachment strips disposed on said wrap for releasably engaging and holding a portion of the intravenous tubing thereon.

5. An intravenous securing device and secondary wound dressing for holding intravenous tubing in place on a variety of anatomic locations on the human body and holding a primary wound l dressing on top of an intravenous needle or catheter inserted into a skin entry site, the needle or catheter connected to the intravenous tubing, the securing device comprising:

an elongated bi-directional wrap having a front side, a back side, a first end and a second end, said wrap stretchable in opposite directions along a length of said wrap;

means for securing the first end of said wrap to the second end of said wrap when said wrap is received around a selected location on the human body;

a window opening in said wrap, a center portion of said window opening adapted for receipt over the skin entry site, said window opening sufficient in size for visual inspection of the skin entry site without having to remove said wrap;

means for holding a portion of the intravenous tubing against the human body and adjacent the skin entry site, said means for holding being a portion of the back side of said elongated wrap and disposed next to said window opening; and intravenous tubing offset holding means for releasably securing a portion of the intravenous tubing on the front side of said wrap and adjacent to and offset from the center portion of said window opening for providing a clear view of the skin entry site, said intravenous tubing offset holding means for releasably securing the intravenous tube substantially parallel to a length of the intravenous needle or catheter inserted into the skin entry site.

6. The securing device as described in claim 5 wherein said intravenous tubing offset holding means is a pair of parallel tubing attachment strips, said strips including hook and loop fasteners.

7. The securing device as described in claim 6 wherein said tubing attachment strips are disposed on opposite sides of said window opening.

8. The securing device as described in claim 6 wherein said tubing attachment strips are disposed adjacent said window opening.

9. The securing device as described in claim 5 further including means for securing the primary wound dressing over said window opening in said elongated wrap.

10. The securing device as described in claim 9 wherein said means for securing the primary wound dressing is at least one hook fastener disposed around a periphery of said window opening for releasably engaging the primary wound dressing.

11. An intravenous securing device and secondary wound dressing for holding intravenous tubing in place on a variety of anatomic locations on the human body and holding a primary wound dressing on top of an intravenous needle or catheter inserted into a skin entry site, the needle or catheter connected to the intravenous tubing, the securing device comprising:

an elongated bi-directional wrap having a front side, a back side, a first end and a second end, said wrap stretchable in opposite directions along a length of said wrap;

means for securing the first end of said wrap to the second end of said wrap when said wrap is received around a selected location on the human body;

a window opening in said wrap, a center portion of said window opening adapted for receipt over the skin entry site, said window opening having a diameter in a range of 1 to 3 inches for visual inspection of the skin entry site without having to remove said wrap;

means for holding a portion of the intravenous tubing against the human body and adjacent the skin entry site, said means for holding being a portion of the back side of said elongated wrap and disposed next to said window opening; and intravenous tubing offset holding means for releasably securing a portion of the intravenous tubing on the front side of said wrap and adjacent to and offset from the center portion of said window opening for providing a clear view of the skin entry site, said intravenous tubing offset holding means for releasably securing the intravenous tube substantially parallel to a length of the intravenous needle or catheter inserted into the skin entry site.

12. The securing device as described in claim 11 wherein said intravenous tubing offset holding means is a pair of tubing attachment strips having hook and loop fasteners.

13. The securing device as described in claim 12 wherein said tubing attachment strips having hook and loop fasteners are disposed on opposite sides of said window opening.

14. The securing device as described in claim 13 wherein said tubing attachment strips having hook and loop fasteners are disposed adjacent said window opening.

15. The securing device as described in claim 11 further including means for securing the primary wound dressing over said window opening in said elongated wrap.

16. The securing device as described in claim 15 wherein said means for securing the primary wound dressing is at least one hook fastener disposed around a periphery of said window opening for releasably engaging the primary wound dressing.

* * * * *

UNITED STATES PATENT AND TRADEMARK OFFICE
CERTIFICATE OF CORRECTION

PATENT NO.   : 5,897,519
DATED        : April 27, 1999
INVENTOR(S)  : Shesol et al It is certified that error appears in the above-identified patent and that said Letters Patent is hereby corrected as shown below:

On the title page: Item [75] Inventors: Delete "Marshall P. Reich" as an inventor.

Signed and Sealed this

First Day of February, 2000

Attest:

Q. TODD DICKINSON

Attesting Officer

Acting Commissioner of Patents and Trademarks